(12) United States Patent
St-Jean et al.

(10) Patent No.: US 10,470,841 B2
(45) Date of Patent: Nov. 12, 2019

(54) ROBOT-BASED RACK PROCESSING SYSTEM

(71) Applicant: STERIS Inc., Temecula, CA (US)

(72) Inventors: Hugo St-Jean, Quebec (CA); Daniel Rochette, Quebec (CA)

(73) Assignee: STERIS Inc., Temecula, CA (US)

( * ) Notice: Subject to any disclaimer, the term of this patent is extended or adjusted under 35 U.S.C. 154(b) by 39 days.

(21) Appl. No.: 15/471,071

(22) Filed: Mar. 28, 2017

(65) Prior Publication Data
US 2018/0280112 A1    Oct. 4, 2018

(51) Int. Cl.
*A61B 90/70* (2016.01)
*B08B 13/00* (2006.01)
(Continued)

(52) U.S. Cl.
CPC .............. *A61B 90/70* (2016.02); *B08B 13/00* (2013.01); *G05D 1/0297* (2013.01); *A61B 50/22* (2016.02);
(Continued)

(58) Field of Classification Search
CPC .............. A61B 1/125; A61B 2017/003; A61B 2034/301; A61B 34/25; A61B 34/30; A61B 34/37; A61B 34/71; A61B 1/123; A61B 2017/00243; A61B 2034/715; A61B 17/062; A61B 2017/00238; A61B 2017/00336; A61B 2017/00743; A61B 2017/00805; A61B 2034/105; A61B 2034/107; A61B 2034/2015;
(Continued)

(56) References Cited

U.S. PATENT DOCUMENTS

| 3,742,738 A | * | 7/1973 | Frotriede | ................ D06F 95/00 |
| | | | | 68/210 |
| 4,328,422 A | | 5/1982 | Loomer | ........................ 250/239 |

(Continued)

FOREIGN PATENT DOCUMENTS

| CA | 2398942 A1 * | 8/2001 | ......... A61B 1/00057 |
| DE | 20023832 U1 | 11/2006 | |

(Continued)

OTHER PUBLICATIONS

Website print out of "Adept Mobile Products," Adept Lynx Omron Adept Technologies, Inc., http://www.adept.com/products/mobilerobots/mobileplatforms/lynx/general, printout date, Mar. 3, 2017.

(Continued)

*Primary Examiner* — Alexander G Kalinowski
*Assistant Examiner* — Sanjeev Malhotra
(74) *Attorney, Agent, or Firm* — Kusner & Jaffe

(57) ABSTRACT

A robot-based system for processing racks used for transportation of articles in connection with an inactivation procedure, such as sterilization, disinfection, and decontamination. Robots are used to move full and empty racks between a plurality of a locations within soiled and clean areas of a workspace, including, but not limited to, a loading station where soiled medical instruments are loaded on the racks, washer/disinfectors for processing the medical instruments, and an unloading station where clean medical instruments are unloaded from the racks for sorting into trays.

6 Claims, 6 Drawing Sheets

(51) Int. Cl.
*G05D 1/02* (2006.01)
*A61B 50/22* (2016.01)

(52) U.S. Cl.
CPC ..... *G05D 2201/0206* (2013.01); *Y10S 901/01* (2013.01)

(58) Field of Classification Search
CPC ........ A61B 2090/364; A61B 2090/376; A61B 2090/378; A61B 34/20; A61B 46/10; A61B 50/13; A61B 8/0808; A61B 90/361; A61B 17/0469; A61B 17/0482; A61B 17/1114; A61B 18/08; A61B 1/00057; A61B 1/018; A61B 1/2676; A61B 1/273; A61B 2017/00296; A61B 2034/102; A61B 2034/2063; A61B 2034/256; A61B 2034/303; A61B 2090/035; A61B 2090/062; A61B 2090/065; A61B 2090/3784; A61B 34/74; A61B 34/76; A61B 5/0006; A61B 5/053; A61B 5/7285; A61B 6/541; A61B 8/12; A61B 90/39; A61B 90/50; A61L 2/24; A61L 2/22; A61L 2202/17; A61L 2202/24; A61L 2/18; A61L 2/186; B33Y 80/00; B33Y 70/00; G01N 35/04; G01N 2035/041; G01N 1/31; G01N 2035/00542; G01N 2035/00851; G01N 2035/0465; G01N 21/78; G01N 33/54386; G01N 35/00623; G01N 35/00732; G01N 35/0092; G01N 35/0099; G01N 35/026; G01N 35/028; G01N 19/00; A61M 25/0133; A61M 2025/0004; A61M 25/0105; A61M 25/0147; B01L 2200/025; B01L 2300/021; B01L 2300/022; B65B 3/003; B65B 31/02; B65B 31/024; B65B 55/16; B65B 59/00; A01B 35/32; A01B 76/00; A61J 1/20; A61J 3/002; B01F 11/0008; B01F 11/0017; B01F 13/0094; B01F 13/1055; B01F 13/1063; B01F 15/00253; B08B 3/02; B25J 11/0085; B25J 5/02; B25J 9/023; B25J 9/1676; B25J 9/1689; G05B 2219/40202; G05B 2219/40425; G05D 1/0265; G05D 2201/0208; G07F 11/002; G07F 11/165; G07F 11/70; Y10S 435/809; Y10S 436/809; Y10S 901/02
USPC ............... 700/226, 230, 239, 245, 248, 299; 73/863.81; 422/28, 50, 65; 435/5, 6.19; 436/47; 414/217, 222.01; 606/1; 134/18, 25.2, 102.2, 161; 172/1; 141/37; 600/106, 407; 424/700; 294/213; 105/156; 296/19; 165/11.1
See application file for complete search history.

(56) References Cited

U.S. PATENT DOCUMENTS

| | | | |
|---|---|---|---|
| 4,500,970 A | 2/1985 | Daemmer | 364/513 |
| 4,679,152 A | 7/1987 | Perdue | 364/513 |
| 5,211,523 A | 5/1993 | Andrada Galan et al. | 414/282 |
| 5,279,672 A | 1/1994 | Betker et al. | 134/18 |
| 5,756,304 A * | 5/1998 | Jovanovich | C12Q 1/04 422/50 |
| 6,082,799 A * | 7/2000 | Marek | B60P 3/14 296/19 |
| 6,278,917 B1 | 8/2001 | Bauer et al. | 701/23 |
| 6,558,620 B1 * | 5/2003 | Sanford | A61B 1/123 134/102.2 |
| 6,582,654 B1 * | 6/2003 | Kral | A61B 1/123 134/161 |
| 6,959,714 B1 | 11/2005 | Håkansson et al. | 134/25.2 |
| 7,114,907 B2 | 10/2006 | Ogawa et al. | 414/744.5 |
| 7,133,746 B2 | 11/2006 | Abramson et al. | 700/259 |
| 7,306,423 B2 | 12/2007 | Ogawa et al. | 414/749.1 |
| 7,708,517 B2 | 5/2010 | Nakamura et al. | 414/816 |
| 7,809,470 B2 | 10/2010 | Shoenfeld | 700/243 |
| 7,850,414 B2 | 12/2010 | Uratani et al. | 414/744.2 |
| 7,996,109 B2 | 8/2011 | Zini et al. | |
| 8,272,830 B2 | 9/2012 | Kurita et al. | 414/749.5 |
| 8,532,817 B2 | 9/2013 | Bacom et al. | 700/214 |
| 8,721,984 B2 | 5/2014 | Carbone et al. | 422/292 |
| 8,795,593 B2 | 8/2014 | Nichols et al. | 422/63 |
| 8,948,914 B2 | 2/2015 | Zini et al. | 700/258 |
| 9,358,688 B2 | 6/2016 | Drew | 52/747 |
| 9,360,300 B2 | 6/2016 | DiBernado et al. | 356/614 |
| 9,422,108 B2 | 8/2016 | Hognaland | B65G 1/0464 |
| 9,489,490 B1 | 11/2016 | Theobald | G06F 19/3462 |
| 2002/0001537 A1 * | 1/2002 | Hlebovy | A61B 1/00057 422/28 |
| 2005/0038556 A1 * | 2/2005 | Gagnon | A61B 90/90 700/226 |
| 2005/0166860 A1 * | 8/2005 | Austin | A01K 1/031 119/458 |
| 2006/0178776 A1 * | 8/2006 | Feingold | G01N 35/0092 700/245 |
| 2006/0276775 A1 * | 12/2006 | Rosenberg | A61B 17/00234 606/1 |
| 2007/0043338 A1 * | 2/2007 | Moll | A61B 34/71 606/1 |
| 2007/0071832 A1 * | 3/2007 | Kral | A61B 1/125 424/700 |
| 2007/0081881 A1 * | 4/2007 | Okuno | H01L 21/67167 414/217 |
| 2007/0099189 A1 * | 5/2007 | Gomez-Elvira Rodriguez | G01N 1/31 435/6.19 |
| 2007/0197896 A1 * | 8/2007 | Moll | A61B 1/00039 600/407 |
| 2010/0043834 A1 * | 2/2010 | Scheringer | A47L 15/241 134/25.2 |
| 2010/0126286 A1 * | 5/2010 | Self | G01N 35/04 73/863.81 |
| 2010/0129789 A1 * | 5/2010 | Self | B01L 9/06 435/5 |
| 2010/0203643 A1 * | 8/2010 | Self | B01L 9/06 436/47 |
| 2011/0067781 A1 * | 3/2011 | Osborne | B65B 3/003 141/37 |
| 2011/0156417 A1 * | 6/2011 | Weber | B65G 45/00 294/213 |
| 2011/0208350 A1 * | 8/2011 | Eliuk | A61J 1/20 700/240 |
| 2011/0262250 A1 * | 10/2011 | Treat | A61L 2/22 414/222.01 |
| 2011/0262319 A1 | 10/2011 | Svensson | |
| 2011/0295423 A1 * | 12/2011 | Anderson | G05D 1/0088 700/248 |
| 2011/0295424 A1 * | 12/2011 | Johnson | A01D 34/008 700/248 |
| 2012/0028342 A1 * | 2/2012 | Ismagilov | B01L 3/502738 435/283.1 |
| 2012/0065467 A1 * | 3/2012 | Moll | A61B 8/12 600/106 |
| 2012/0291808 A1 * | 11/2012 | Monsrud | B08B 3/02 134/18 |
| 2013/0184849 A1 | 7/2013 | Chan | 700/113 |
| 2014/0014292 A1 * | 1/2014 | Rice | H05K 7/20836 165/11.1 |
| 2014/0144470 A1 * | 5/2014 | Sewell | B01F 3/04503 134/18 |
| 2014/0241946 A1 * | 8/2014 | Self | G01N 35/04 422/65 |
| 2014/0246257 A1 | 9/2014 | Jacobsen et al. | 180/14.2 |

(56) References Cited

U.S. PATENT DOCUMENTS

| | | | |
|---|---|---|---|
| 2014/0365258 A1 | 12/2014 | Vestal et al. ................. 705/7.15 |
| 2015/0241458 A1* | 8/2015 | Pollack ............ G01N 35/00623 |
| | | | 700/230 |
| 2015/0250678 A1* | 9/2015 | Eliuk ........................ A61J 1/20 |
| | | | 700/239 |
| 2015/0273691 A1* | 10/2015 | Pollack ............ G01N 35/00623 |
| | | | 348/143 |
| 2015/0337400 A1* | 11/2015 | Wilson ................... G16B 99/00 |
| | | | 700/299 |
| 2015/0351309 A1* | 12/2015 | Gaus .................... A01B 51/023 |
| | | | 172/1 |
| 2016/0158942 A1 | 6/2016 | Augenbraun et al. ........ 700/253 |
| 2016/0235879 A1 | 8/2016 | Andersson et al. |
| 2016/0236869 A1 | 8/2016 | Kimura et al. ...... B65G 1/1378 |
| 2016/0288121 A1* | 10/2016 | Ismagilov ......... B01L 3/502738 |
| 2017/0086929 A1* | 3/2017 | Moll ........................ A61B 8/12 |
| 2017/0251589 A1* | 9/2017 | Tippery ................. A01G 22/00 |
| 2018/0036889 A1* | 2/2018 | Birkmeyer .......... A47L 15/4293 |
| 2018/0318458 A1 | 11/2018 | Rasmussen |

FOREIGN PATENT DOCUMENTS

| | | | |
|---|---|---|---|
| DK | 201600071 U3 | 2/2017 | |
| WO | WO-2007089269 A2 * | 8/2007 | ................ B25J 5/02 |
| WO | WO-2016009204 A1 * | 1/2016 | ............. A61B 50/34 |
| WO | WO-2017163251 A2 * | 9/2017 | ............ B25J 9/1676 |

OTHER PUBLICATIONS

KEN Hygiene Systems, Automated Logistics Product Brochure, "KEN AL10, Automated load carrier for instrument trolleys in CSSD departments," 2017.

\* cited by examiner

ROBOT-BASED RACK PROCESSING SYSTEM

FIELD OF THE INVENTION

The present invention relates to a robot-based system for processing racks used for transportation of articles in connection with an inactivation procedure, such as a sterilization, disinfection, or decontamination process.

BACKGROUND OF THE INVENTION

In many healthcare facilities (e.g., hospitals), a central sterilization services department (CSSD) is responsible for carrying out inactivation procedures (e.g., sterilization, disinfection, and decontamination) on medical utensils, surgical instruments, and other articles found in the healthcare facility (collectively referred to herein as "medical instruments"). The workspace for a conventional CSSD is physically arranged such that there is (i) a soiled area and (ii) a clean area which is isolated from the soiled area. Soiled medical instruments are loaded into an inactivation apparatus (such as a disinfector/washer or sterilizer) in the soiled area, and the processed medical instruments are unloaded from the inactivation apparatus in the clean area.

A rack (e.g., a manifold rack) is used to facilitate transportation and processing of the medical instruments within the workspace of the CSSD. At a first location (within the soiled area), soiled medical instruments are loaded onto a rack. Subsequently, the full rack is moved to a second location (within the soiled area) for loading into an inactivation apparatus. When the inactivation procedure is completed, the full rack is unloaded from the inactivation apparatus at a third location (within the clean area), and moved to a fourth location (within the clean area) where the medical instruments are unloaded from the rack. The empty rack is then returned to the soiled area for reuse.

In prior art rack processing systems used in connection with washers/disinfectors, it is known to use automation to load racks into the washer/disinfector and to unload racks from the washer/disinfector. However, in the prior art, transfer carts are used to manually transport racks between the location where racks are loaded with the soiled medical instruments and the location of an automated loader or conveyer used to load racks into the washer/disinfector. Transfer carts are also used by operators to manually transport a rack between the location of an automated unloader or conveyer that receives a rack unloaded from the washer/disinfector and the location where the medical instruments are unloaded from the rack.

The present invention overcomes these and other drawbacks of the prior art by providing a robot-based system for processing racks used for transportation of articles in connection with an inactivation procedure.

SUMMARY OF THE INVENTION

In accordance with the present invention, there is provided a rack processing system for processing racks in a workspace having a soiled area and a clean area isolated from the soiled area, the rack processing system comprising: at least one inactivation apparatus for carrying out an inactivation procedure, said inactivation apparatus loaded in the soiled area and unloaded in the clean area; a first robot located in the soiled area for transporting a rack loaded with soiled medical instruments from a first location in the soiled area to the at least one inactivation apparatus; a second robot located in the clean area for transporting a rack loaded with clean medical instruments from the at least one inactivation apparatus to a second location in the clean area; and a central computer system for providing instructions to the first and second robots.

In accordance with another aspect of the present invention, there is provided a method for processing racks in a workspace having a soiled area and a clean area isolated from the soiled area, the method comprising: transmitting a pick up request from a loading station to a central computer system, the pick up request requesting pick up of a full rack from the loading station; and determining whether an inactivation apparatus is available for processing a rack, wherein if an inactivation apparatus is available, then transmitting instructions from the central computer system to a first robot located in the soiled area to pick up the full rack from the loading station and transport it to the available inactivation apparatus, and if the inactivation apparatus is not available, then transmitting instructions from the central computer system to the first robot to pick up the full rack from the loading station and transport it to a first buffer storage.

An advantage of the present invention is the provision of a rack processing system having greater levels of automation.

Another advantage of the present invention is the provision of a rack processing system having improved logistics.

Still another advantage of the present invention is the provision of a rack processing system that provides faster and more efficient processing.

A still further advantage of the present invention is the provision of a rack processing system that can reduce injury risk to the operator.

Yet another advantage of the present invention is the provision of a rack processing system that integrates use of autonomously guided vehicles for transport of racks within a workspace.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE INVENTION

Figure 1:
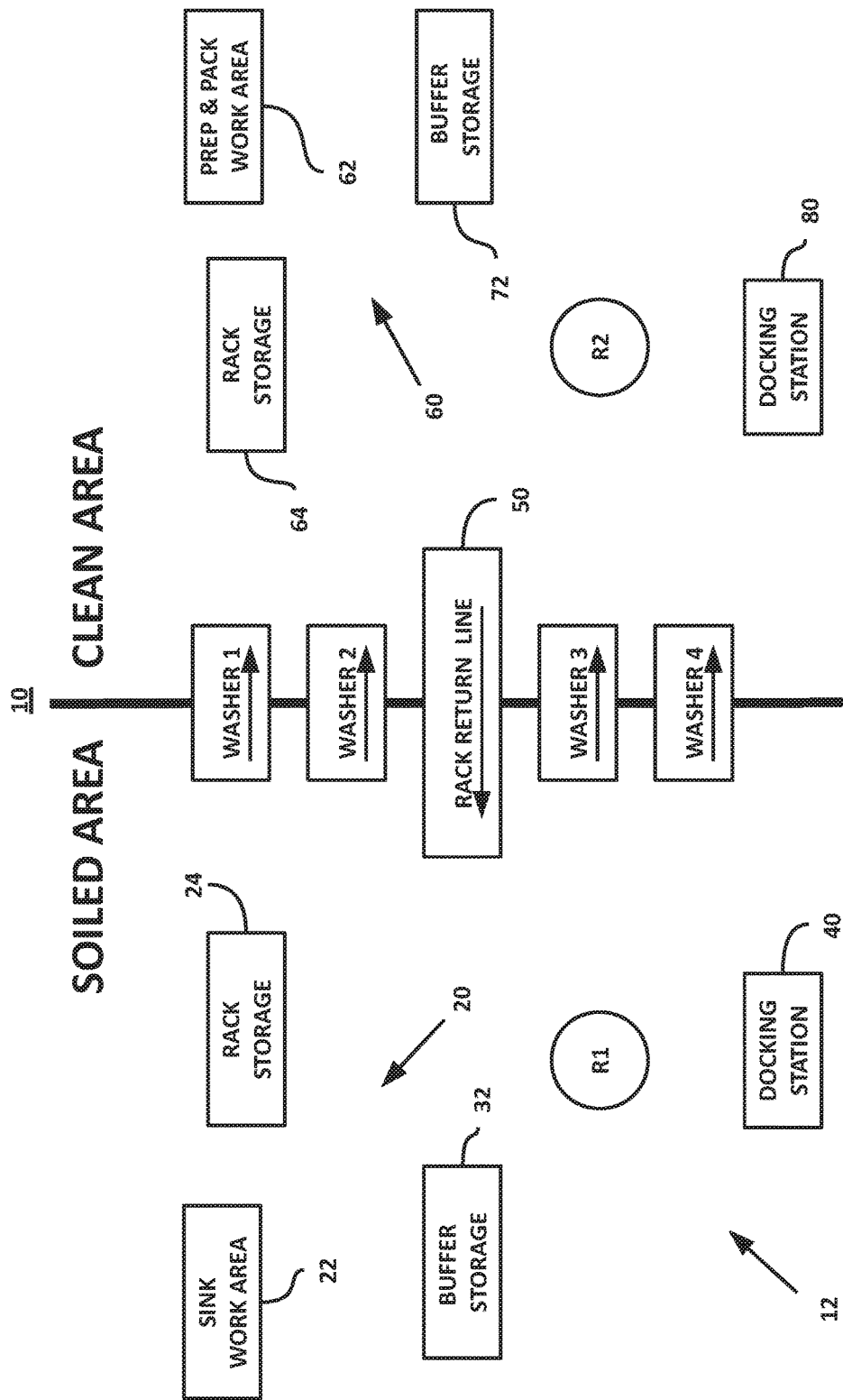
FIG. 1 is a block diagram of a workspace for a robot-based rack processing system, according to an embodiment of the present invention.

Referring now to the drawings wherein the showings are for the purposes of illustrating an embodiment of the present invention only and not for the purposes of limiting same, FIG. 1 shows a block diagram of a workspace 10 for a robot-based rack processing system 12, according to an embodiment of the present invention. Workspace 10 is divided into a soiled area and a clean area that is isolated from the clean area by a wall or other barrier.

It should be appreciated that the present invention is described herein with reference to a disinfection procedure that uses washer/disinfectors as the disinfection apparatus, as will be described below. However, this illustrated embodiment of the present invention is not intended to limit same. Thus, it is contemplated that other types of inactivation apparatus may be substituted for the washer/disinfectors of the illustrated embodiment, including, but not limited to, a sterilization apparatus. Moreover, the operations described herein as pre-wash and post-wash may be other types of processing steps taken before and after a different inactivation procedure (e.g., sterilization).

In the soiled area of workspace 10, system 12 is generally comprised of a loading station 20, a buffer storage 32, a docking station 40, and a robot R1. Loading station 20 includes a sink work area 22 and a rack storage 24. In the clean area of workspace 10, system 12 is generally comprised of an unloading station 60, a buffer storage 72, a docking station 80, and a robot R2. Unloading station 60 includes a preparation and packaging ("prep & pack") work area 62 and a rack storage 64.

System 12 also includes one or more inactivation apparatus and a rack return line 50. A loading side of the inactivation apparatus is located in the soiled area, and an unloading side of the inactivation apparatus is located in the clean area. In the illustrated embodiment, the inactivation apparatus takes the form of washers 1-4, which are conventional washer/disinfectors which both wash and disinfect medical instruments. For example, the washer/disinfectors may be Reliance® or AMSCO® brand washer/disinfectors from STERIS. A loading side of the rack return line 50 is located in the clean area and an unloading side of rack return line 50 is located in the soiled area. In the illustrated embodiment, rack return line 50 takes the form of a conventional conveyor system.

Loading station 20, buffer storage 32, docking station 40, washers 1-4, and rack return line 50 are locations between robot R1 moves to deliver and retrieve racks, as will be described in detail below. It is contemplated that robot R1 may travel to additional locations within the soiled area that are not shown in the illustrated embodiment.

Referring now to the soiled area of workspace 10, loading station 20 is a location where an operator performs pre-wash operations to process soiled medical instruments. Sink work area 22 includes one or more washing sinks. Rack storage 24 is a structure for storing (i) empty racks that are to be filled by an operator with pre-washed medical instruments and (ii) storing racks that have been filled by an operator with pre-washed medical instruments to be processed by a washer. In the illustrated embodiment, rack storage 24 may take the form of one or more tables located proximate to washing sinks in sink work area 22. Buffer storage 32 provides temporary storage for full racks that are awaiting loading into a washer. In the illustrated embodiment, buffer storage 32 may take the form of one or more tables or shelves.

In the illustrated embodiment, robot R1 is an autonomous guided vehicle (AGV), such as the Adept Lynx™ self-navigating autonomous indoor vehicle (AIV) from Omron Adept Technologies, Inc. The Adept Lynx™ includes a controller, a user interface (e.g., touchscreen interface), an electric motor locomotion system, an on-board power supply (22-29 VDC power pack), power management, I/O for wireless communication, sensors, lasers support, and a programmable navigation system for navigating through the use of a stored digital map. Robot R1 can use the digital map to avoid traveling into regions within workspace 10, such as a region proximate to a washer undergoing maintenance. For example, Robot R1 can be programmed to prevent entry into certain prohibited regions within workspace 10.

In the illustrated embodiment, robot R1 may be adapted to include a computer controlled payload handling system to facilitate the handling, loading, and unloading of racks from robot R1. The handling system includes a support platform for supporting a rack on robot R1; an alignment system for precise alignment of robot R1 at a target location; a lift system for adjusting the vertical position of the support platform; and a pusher/puller system for "pushing" a rack off of the support platform and for "pulling" a rack onto the support platform. The lift system is comprised of a motor (e.g., servomotor), a scissor lift assembly, and a limit switch. The pusher/puller system is comprised of a motor (e.g., servomotor), an actuator (e.g., a solenoid), and a limit switch. The alignment system includes one or more proximity sensors and one or more lasers.

The handling system operates in the following manner. The laser is used to detect the center position of a goal (e.g., the loading-side or unloading-side opening of a washer) using a target. The target may take the form of a vertical narrow reflector strip that reflects the laser beam while robot R1 is turning a few degrees for a laser scan. Robot R1 turns in order to accurately align with the center position of the goal. The robot then moves forward toward the goal until the proximity sensors detect contact with the surface of the goal. Once robot R1 has reached the goal, the height of the support platform is adjusted by the lift system using the same laser beam. In this regard, the lift system increases the height of the support platform, until it detected that the laser beam has reached the top of the reflector strip.

In accordance with an embodiment of the present invention, the support platform includes a sensor and a plunger. The plunger holds the rack in place during movement of the robot, and the sensor detects whether the rack has been successfully loaded onto the support platform.

Robot R1 may also include a fluid collection system that includes a fluid collection reservoir (e.g., drip pan) and an electronically actuated drain valve. The fluid collection reservoir collects water that drips off the racks transported by robot R1. For example, water or condensate may be on the surface of the racks as a result of the washing/disinfection process. The drain valve is opened to empty the fluid collection reservoir. The fluid collection system may also include a level detector for detecting the fluid level within the fluid collection reservoir. The level detector alerts the control system of robot R1 that the fluid collection reservoir needs to be purged. This information can also be communicated to a central computer system 100, described below.

Docking station 40 serves as a recharging station that provides power for recharging a battery of robot R1. In the illustrated embodiment, docking station 40 may also include a floor drain or a collection vessel for receiving fluid emptied from the fluid collection reservoir of robot R1.

Referring now to the clean area of workspace 10, unloading station 60 is a location where an operator performs post-wash operations. At prep & pack work area 62, an operator unloads clean medical instruments from a rack, inspects the medical instruments, and sort the medical instruments into organized trays. The organized trays may be stored in a cooling storage unit (not shown). Rack storage 64 is a structure for storing (i) full racks that have been removed from a washer and are to be processed by an operator and (ii) racks that have been emptied by an operator and are awaiting return to the soiled area. In the illustrated embodiment, rack storage 64 may take the form of one or more tables located proximate to prep & pack work area 62. Buffer storage 72 provides temporary storage for full racks that have been removed from a washer. In the illustrated embodiment, buffer storage 32 may take the form of one or more tables or shelves.

Unloading station 60, buffer storage 72, docking station 80, washers 1-4, and rack return line 50 are locations between robot R2 moves to deliver and retrieve racks, as will be described in detail below. It is contemplated that robot R2 may travel to additional locations within the clean area that are not shown in the illustrated embodiment.

Robot R2 is substantially the same as robot R1 described above. Likewise, docking station 80 is substantially the same as docking station 40 described above.

It should be appreciated that while the illustrated embodiment of the present invention has only a single robot in the soiled and clean areas, it is contemplated that a more than one robot may be located in the soiled and clean areas.

Figure 2:
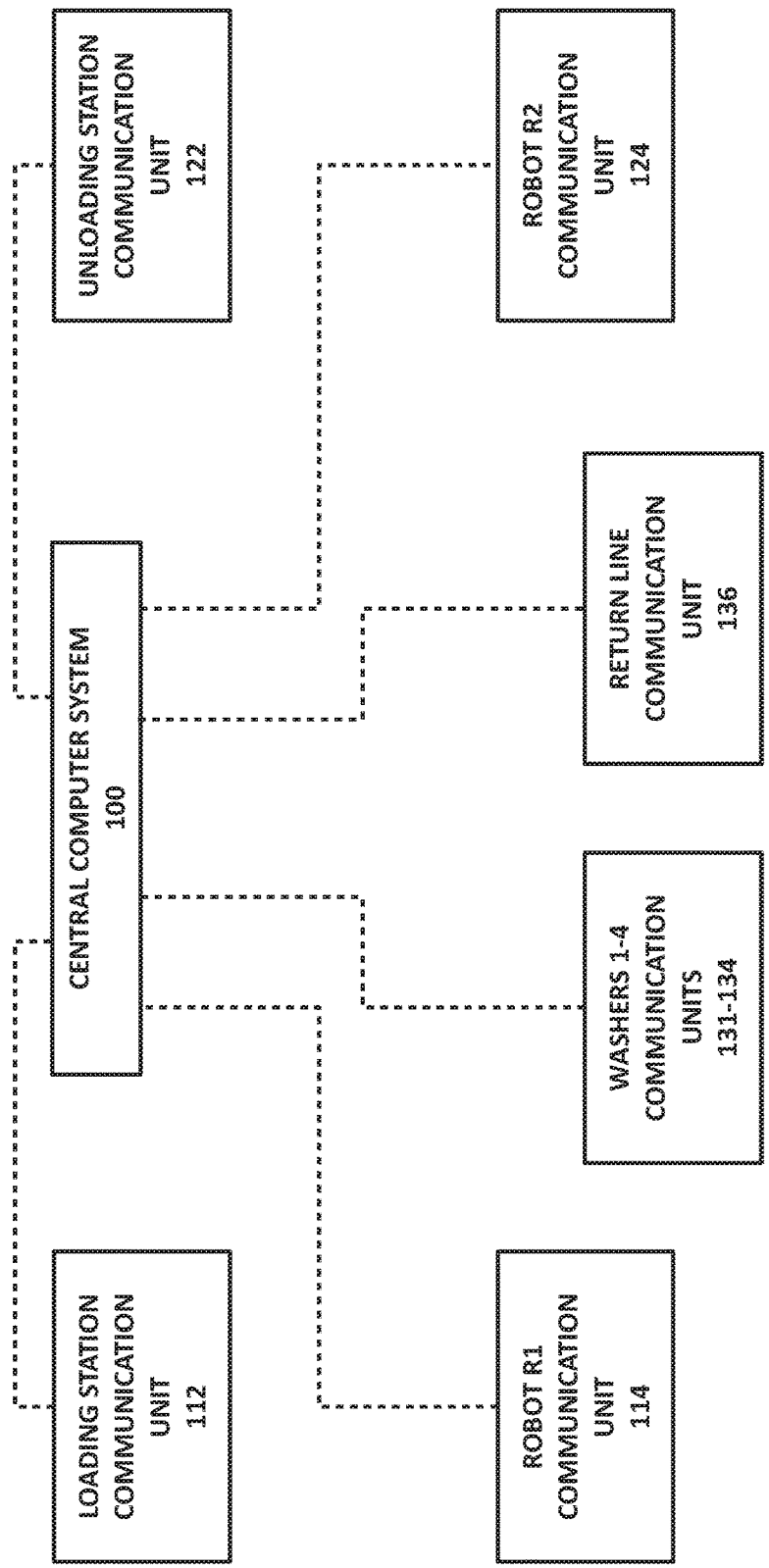
FIG. 2 is a block diagram of a central computer system of the rack processing system as linked to several associated communication units, according to an embodiment of the present invention.

System 12 also includes central computer system 100, as shown in FIG. 2. Communication units located within the soiled and clean areas allow for bi-directional data communication with central computer system 100. Communication between central computer system 100 and the communication units may include the use wired and/or wireless communication systems (e.g., Ethernet, TCP/IP, Wi-Fi, etc.).

In the illustrated embodiment, loading station communication unit 112 and unloading station communication unit 122 include a user interface for an operator to request a rack pick up or delivery. For example, a tablet computer device may serve as communication units 112 and 122. Robot R1 includes communication unit 114 and robot R2 includes communication unit 124. Washers 1-4 include communication units 131-134 to provide status information to the central computer system 100 (e.g., ready for loading, busy, and cleaning cycle complete) and to receive instructions from central computer system 100 (e.g., open door at soiled-side for loading, and open door at clean-side for unloading), and rack return line 50 includes communication unit 136 to provide status information (e.g., rack awaiting pick up at soiled-side).

In an embodiment of the present invention, the racks of system 12 may include a machine-readable code (e.g., bar code or RFID tag) that can be scanned. The machine-readable code can uniquely identify each rack and/or identify a rack type (e.g., 2-level rack, 5-level rack, multi-function rack, special purpose rack, etc.). Each washer 1-4 may include a scanner to scan each rack that is loaded into the washer. The information about the scanned rack is communicated by washers 1-4 (via communication units 131-134) to central computer system 100. Information about the scanned rack can be used by the washer to determine a suitable cleaning cycle for the rack. Rack return line 50 may also include a scanner to scan each rack that is returned from the clean area to the soiled area. Information about each rack is communicated by return line 50 (via communication unit 136) to central computer system 100. Accordingly, central computer system 100 can prioritize a rack pick up at return line 50 (soiled area) based upon a requested rack type. It is also contemplated that robots R1 and R2 may include scanners to scan racks, and provide information about the racks to central computer system 100.

Basic operation of robot-based rack processing system 10, according to an embodiment of the present invention, will now be summarized in connection with rack processing in the soiled and clean areas.

Soiled Area

1) An operator at loading station 20 sends instructions to central computer system 100 requesting pick up of a full rack loading station 20, and delivery of an empty rack to loading station 20.
2) Robot R1 receives instructions from central computer system 100 to pick up the full rack at loading station 20, and delivery the full rack to an available washer. If no washers are currently available, then robot R1 delivers the full rack to buffer storage 32 for temporary storage until a washer becomes available.
3) Robot R1 receives instructions from central computer system 100 to pick up an empty rack from the rack return line 50 and deliver the empty rack to loading station 20.

Clean Area

1) An operator at unloading station 60 sends instructions to central computer system 100 requesting pick up of an empty rack at unloading station 60, and delivery of a (clean) full rack to unloading station 60.
2) Robot R2 receives instructions from central computer system 100 to pick up an empty rack from unloading station 60 and deliver the empty rack to rack return line 50 for return to the soiled area of workspace 10.
3) Robot R2 receives instructions from central computer system 100 to pick up the (clean) full rack at one of the washers, and deliver the full rack to unloading station 60. If no space is available at unloading station 60, then robot R2 delivers the full rack to buffer storage 72 for temporary storage until space becomes available at unloading station 60.

Detailed operation of robot-based rack processing system 12 will now be described with reference to FIGS. 3-7, which respectively illustrate flow diagrams for a pre-wash pick up routine 150, a washer load routine 170, a washer unload routine 190, a buffer storage unload routine 210, and an unloading station pick up routine 230.

Figure 3:
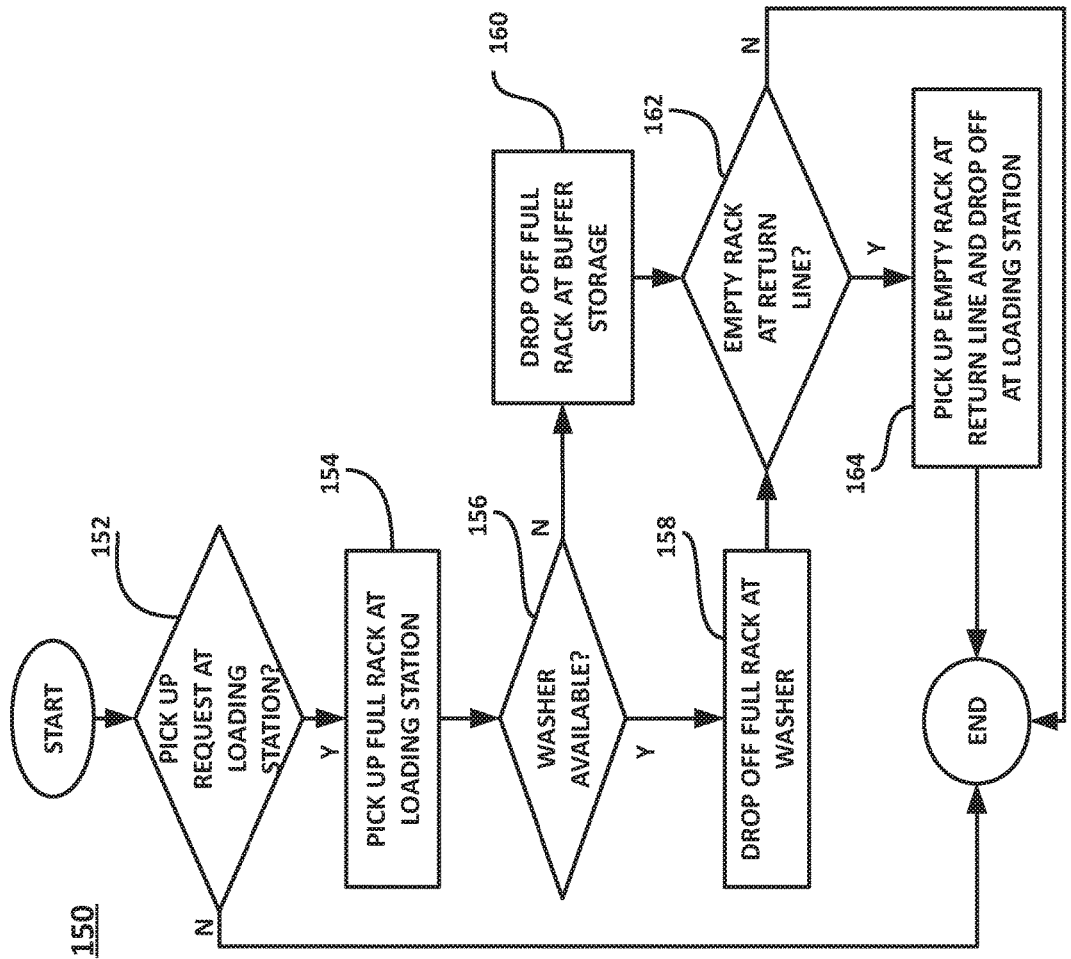
FIG. 3 is a flow diagram illustrating a pre-wash pick up routine, according to an embodiment of the present invention.

FIG. 3 shows a flow diagram for pre-wash pick up routine 150 (soiled area). This routine involves pick up of a full rack from loading station 20, drop off of the full rack at an available washer or at buffer storage 32, and drop off of an empty rack (returned from the clean area) at loading station 20. First, it is determined whether an operator at loading station 20 has made a pickup request by sending instructions to central computer system 100 (step 152). If a pickup request has been made, then central computer system 100 sends instructions to robot R1 to pick up a full rack at loading station 20 (step 154). The computer system 100 determines whether any washers are available (step 156). If it is determined that no washers are available, then central computer system 100 sends instructions to robot R1 to drop off the full rack at buffer storage 32. If it is determined that a washer is available, then central computer system 100 sends instructions to robot R1 to drop off the full rack at the available washer (step 158). Following the step of dropping off the full rack at a washer (step 158) or the step of dropping off the full rack at buffer storage 32 (step 160), central computer system 100 determines whether there is an empty rack ready for pick up at return line 50 to replace the full rack that was retrieved from loading station 20 (step 162). If it is determined that there is an empty rack awaiting pick up at return line 50, then central computer system 100 sends instructions to robot R1 to pick up the empty rack at return line 50 and drop it off at loading station 20 (step 164). If it is determined that there is no empty rack at return line 50, then the pre-wash pick up routine ends.

In one embodiment of the present invention, central computer system 100 randomly selects an available washer for loading with a full rack. In an alternative embodiment, central computer system 100 selects a washer that is most suitable for the type of rack.

Figure 4:
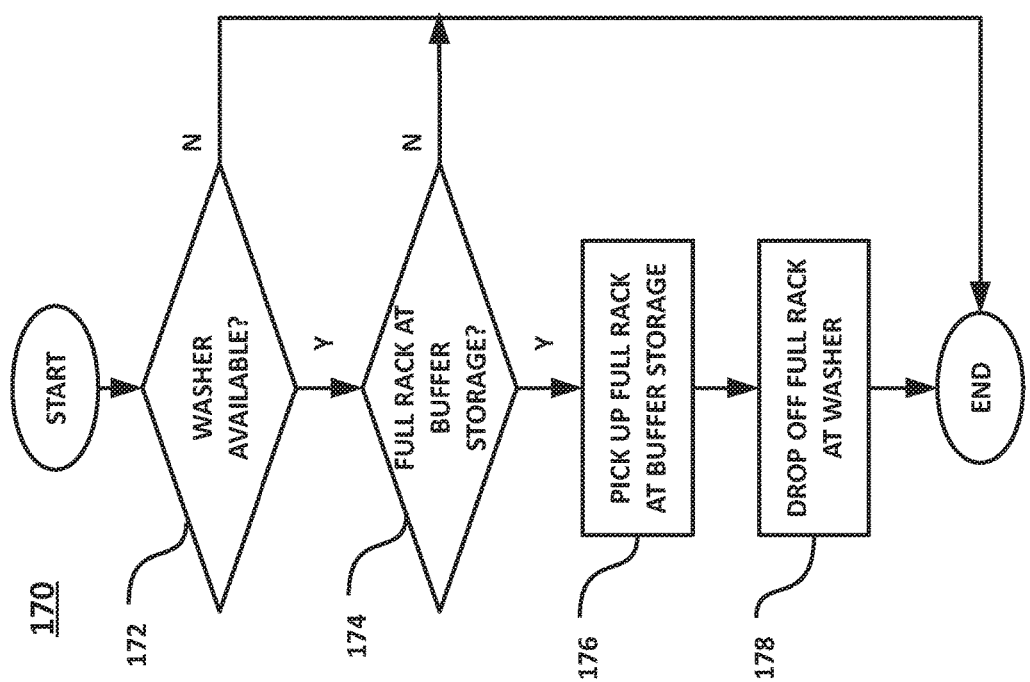
FIG. 4 is a flow diagram illustrating a washer load routine, according to an embodiment of the present invention.

FIG. 4 shows a flow diagram for the washer load routine 170 (soiled area). This routine involves pick up of full rack stored at buffer storage 32 and drop off at an available washer. Central computer system 100 determines whether a washer is available (step 172). If no washer is available, then washer load routine 170 ends. If a washer is available, then it is determined whether there is a full rack awaiting pick up at buffer storage 32 (step 174). If there is no full rack awaiting pick up at buffer storage 32, then washer load routine 170 ends. If there is a full rack awaiting pickup a buffer storage 32, then central computer system 100 sends instructions to robot R1 to pick up a full rack at buffer storage 32 (step 176) and drop off the full rack at the available washer (step 178).

Figure 5:
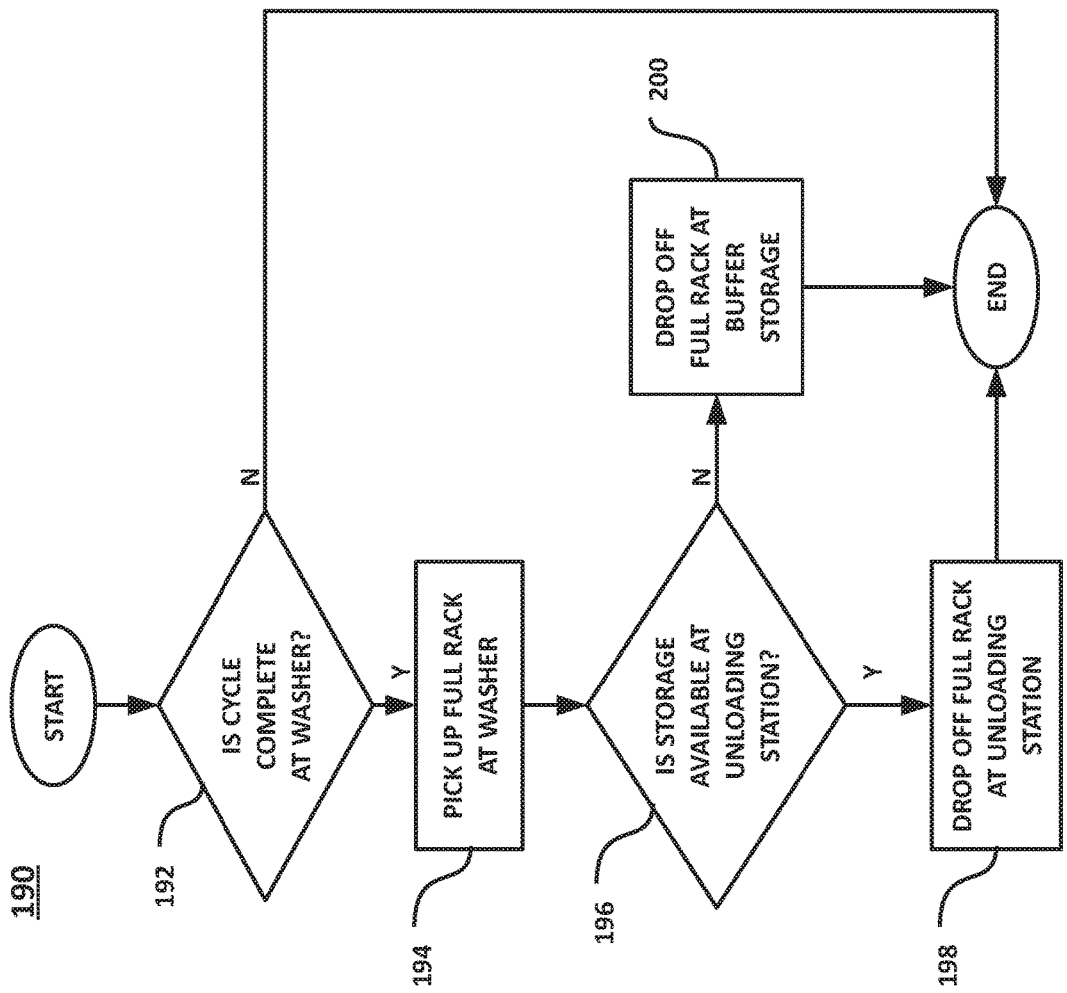
FIG. 5 is a flow diagram illustrating a washer unload routine, according to an embodiment of the present invention.

FIG. 5 shows a flow diagram for the washer unload routine 170 (clean area). This routine involves pick up of a full rack at a washer and drop off of the full rack at unloading station 60 or at buffer storage 72. Central computer system 100 determines if a cleaning cycle is completed at one of the washers 1-4 (step 192). If none of the washers are ready for a pick up, then the washer unload routine 190 ends. If one of the washers 1-4 is ready for a pickup, then central computer system 100 sends instructions to robot R2 to pick up a full rack at the washer (step 194). Central computer system 100 determines whether any storage is available at unloading station 60. If storage is available, then central computer system 100 sends instructions to robot R2 to drop off the full rack at unloading station 60. If no storage is available at unloading station 60, then central computer system 100 sends instructions to robot R2 to drop off the full rack at buffer storage 72 (step 200).

Figure 6:
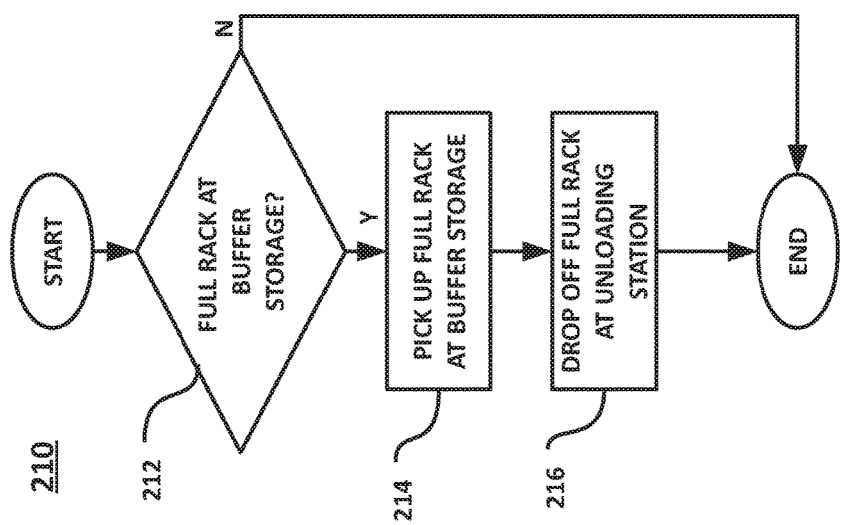
FIG. 6 is a flow diagram illustrating a buffer storage unload routine, according to an embodiment of the present invention.

FIG. 6 shows a flow diagram for the buffer storage unload routine 210 (clean area). This routine involves pick up of a full rack at buffer storage 72 and drop off of the full rack at unloading station 60. Central computer system 100 determines if a full rack is awaiting pickup at buffer storage 72 (step 212). If no full rack is awaiting pickup, then buffer storage unload routine 210 ends. If a full rack is awaiting pickup, then central computer system 100 sends instructions to robot R2 to pick up the full rack at buffer storage 72 (step 214) and drop off the full rack at unloading station 60 (step 216).

Figure 7:
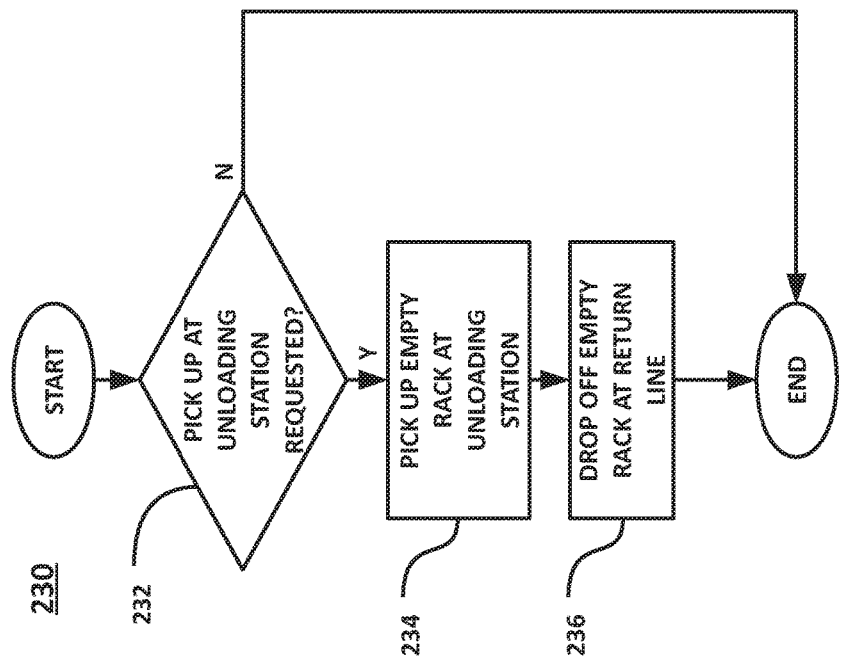
FIG. 7 is a flow diagram illustrating an unloading station pick up routine, according to an embodiment of the present invention.

FIG. 7 shows a flow diagram for the unloading station pick up routine 230 (clean area). This routine involves pick up of an empty rack at unloading station 60 and drop off of the empty rack at return line 50. Central computer system 100 determines whether an operator has made a request for a pickup at unloading station 60 (step 232). If a pickup request has been made, then central computer system 100 sends instructions to robot R2 to pick up the empty rack at unloading station 60 (step 234) and drop off the empty rack at return line 50 (step 236). If no pickup request has been made by an operator, then unloading station pick up routine 230 ends.

In one embodiment of the present invention, the instructions sent to central computer system 100 by the operator to request pick up of a full rack at loading station 20 may include (i) a priority level to identify a priority for the requested pick up of the full rack, and/or (ii) a rack-type to identify the type of empty rack that is to be delivered to loading station 20 to replace the full rack being picked up. In one embodiment of the present invention, priority levels are represented by a value from 1 to 100, where 1 is normal priority and 100 is highest priority.

It is also contemplated that a priority level and/or a rack-type may be determined by central computer system 100 for complete processing by system 12. For example, priority level and rack-type may be determined according to a list of surgery requests entered into central computer system 100. Therefore, depending on the type of surgeries scheduled for the day, certain medical instruments may need to be processed by the washers faster than others in order to be available for use in the next scheduled surgery. This priority level selection allows a high priority level to be associated with a particular rack type.

The foregoing describes specific embodiment of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A rack processing system for processing racks in a workspace having a soiled area and a clean area isolated from the soiled area, the rack processing system comprising:
   a loading station in the soiled area for loading racks with soiled medical instruments;
   a first buffer storage in the soiled area for storing racks loaded with soiled medical instruments;
   at least one inactivation apparatus for carrying out an inactivation procedure on racks loaded with soiled medical instruments, said inactivation apparatus is a washer/disinfector or a sterilizer having a loading side in the soiled area and an unloading side in the clean area;
   a rack return line including a conveyer for returning racks from the clean area to the soiled area, said rack return line having a loading side in the clean area and an unloading side in the soiled area;
   a first robot located in the soiled area for transporting racks between a plurality of locations that include: (i) the loading station, (ii) the first buffer storage, (iii) the inactivation apparatus, and (iv) the rack return line;
   an unloading station in the clean area for unloading medical instruments from racks processed by the inactivation apparatus;
   a second buffer storage in the clean area for storing racks loaded with medical instruments processed by the inactivation apparatus;

a second robot located in the clean area for transporting racks between a plurality of locations that include: (i) the inactivation apparatus, (ii) the unloading station, (iii) the second buffer storage, and (iv) the rack return line; and a central computer system for providing instructions to the first and second robots, the central computer system programmed to:

(a) receive a pick up request from the loading station requesting pick up of a rack from the loading station, and determine whether an inactivation apparatus is available for processing the rack, wherein if the inactivation apparatus is available, the central computer system programmed to transmit instructions to the first robot to pick up the rack from the loading station and transport the rack to the inactivation apparatus that is available, and if the inactivation apparatus is not available, the central computer system programmed to transmit instructions to the first robot to pick up the rack from the loading station and transport the rack to the first buffer storage; and (b) receive status information indicating whether the inactivation apparatus has completed a processing cycle, and determine whether storage is available at the unloading station, wherein if the processing cycle of the inactivation apparatus is complete and storage is available at the unloading station, then the central computer system programmed to transmit instructions from the central computer system to the second robot to pick up the rack from the inactivation apparatus and transport the rack to the unloading station, and if the processing cycle of the inactivation apparatus is complete and storage is not available at the unloading station, then the central computer system programmed to transmit instructions from the central computer system to the second robot to pick up the rack from the inactivation apparatus and transport the rack to the second buffer storage.

2. The rack processing system of claim 1, wherein the system further comprises a first docking station in the soiled area for recharging the first robot.

3. The rack processing system of claim 1, wherein the system further comprises a second docking station in the clean area for recharging the second robot.

4. The rack processing system of claim 1, wherein the central computer system is programmed to determine whether an inactivation apparatus is available for processing a rack and whether a rack is located at the first buffer storage, wherein if the inactivation apparatus is determined to be available and the rack is located at the first buffer storage, said central computer system programmed to transmit instructions to the first robot to pick up the rack from the first buffer storage and transport to the available inactivation apparatus.

5. The rack processing system of claim 1, wherein the central computer system is programmed to determine whether a full rack is located at a second buffer storage, wherein if the full rack is located at the second buffer storage, said central computer system programmed to transmit instructions to the second robot to pick up the full rack from the second buffer storage and transport the full rack to the unloading station.

6. The rack processing system of claim 1, wherein the central computer system is programmed to determine whether a request has been received from the unloading station for a pick up of an empty rack at the unloading station, wherein if the request has been received from the unloading station, said central computer system programmed to transmit instructions to the second robot to pick up the empty rack at the unloading station and transport the empty rack to the return line for returning the empty rack to the soiled area.

* * * * *